United States Patent [19]

Wallshein

[11] 4,219,617
[45] Aug. 26, 1980

[54] CERAMIC ORTHODONTIC BRACKET

[76] Inventor: Melvin Wallshein, 8645 Bay Pkwy., Brooklyn, N.Y. 11214

[21] Appl. No.: 932,290

[22] Filed: Aug. 9, 1978

[51] Int. Cl.³ ............................................. A61C 7/00
[52] U.S. Cl. ......................................................... 433/8
[58] Field of Search ........................... 32/16 A; 433/8

[56] References Cited

U.S. PATENT DOCUMENTS

| | | | |
|---|---|---|---|
| 3,085,336 | 4/1963 | Kesling | 32/16 A |
| 3,504,438 | 4/1970 | Wittman et al. | 32/16 A |
| 3,765,091 | 10/1973 | Northcutt | 32/16 A |

*Primary Examiner*—Robert Peshock
*Attorney, Agent, or Firm*—Frishauf, Holtz, Goodman & Woodward

[57] ABSTRACT

Ceramic orthodontic brackets are disclosed. The brackets are fabricated from high alumina ceramic materials and, in preferred embodiments, have holes or grooves on the back or rear surfaces thereof to improve adhesion to the teeth. Light wire brackets are also disclosed which is substantially wider than prior art light wire brackets, but which comprise means defining a substantially point contact for an arch wire.

29 Claims, 14 Drawing Figures

CERAMIC ORTHODONTIC BRACKET

BACKGROUND OF THE INVENTION

The present invention is directed to orthodontic brackets and, particularly, to brackets having improved characteristics and made of ceramic materials.

The brackets which are used in orthodontic work, and specifically attached to a tooth and joined to other teeth via wires which interconnect with the brackets, are basic to orthodontic dentistry. These brackets have severe and sometimes conflicting service requirements. It is preferable that they have satisfactory asthetic appearance which generally requires white or off-white color. They must have sufficiently high mechanical properties to withstand the severe mechanical stresses placed upon them in use. They must have sufficient abrasion resistance so that they are not unduly abraded by the wires or by contact with food during chewing. They must also be resistant to the fluids in the oral cavity, which resistance would best be achieved by having a bracket which is nonporous or of minimal porosity. It is also necessary that the bracket have suitable characteristics so that it may be adhered to the tooth. Since good adhesion often involves providing a porous bonding surface, this surface requirement is sometimes in conflict with the desirability of the bracket to otherwise have minimal porosity.

Traditionally, brackets have been formed from metals. Metals suffer the disadvantage of their unsightly appearance on teeth. Attempts have been made to overcome this disadvantage by coating the metal, e.g., as disclosed in U.S. Pat. No. 4,050,156. Coating techniques suffer a number of disadvantages, including the tendency for coatings to chip or flake off if they are sufficiently hard to have good abrasion resistance and the tendency for coatings which have good adhesion to be poor in abrasion resistance. Plastic brackets have also been utilized. While plastic brackets have a satisfactory asthetic appearance, they generally have the disadvantage of poor mechanical properties and some difficulties in manufacture.

The object of the present invention is to provide for improved orthodontic brackets having satisfactory asthetic appearance, satisfactory mechanical properties and which are suitable for practical manufacture from ceramic materials.

SUMMARY OF THE INVENTION

In accordance with the present invention, a ceramic orthodontic bracket comprises a shaped article having a first surface adapted to be affixed to a surface of a tooth, the side of said article which is opposed to said first surface having a grooved indentation therein for receiving an arch wire, or the like, the article further having at least two outwardly extending lugs, said ceramic bracket being, preferably white in color and having a tensile strength of at least about 15,000 psi, a modulus of elasticity in excess of about $15 \times 10^6$ psi, a Charpy impact resistance of at least about 5, and a hardness of at least about 9 on the Mohs scale.

DETAILED DESCRIPTION

Figure 1:
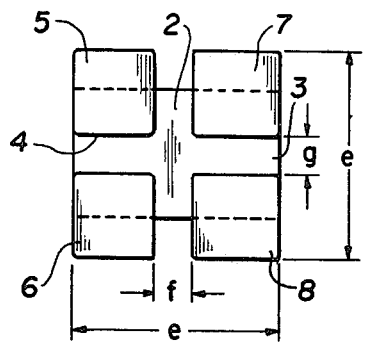
FIG. 1 is a front view of a ceramic orthodontic bracket of the present invention.

Referring to FIGS. 1-4, a ceramic orthodontic "twin" bracket according to the present invention has a curved rear surface 1 which is so curved as to approximately conform to the curvature of the outer surface of a tooth. The ceramic bracket has a base portion 2 and an upper portion 3, the upper portion 3 substantially defining an arch wire receiving slot 4 in the bracket. The upper portion of the bracket 3 is comprised of four generally rectangular portions 5, 6, 7, 8 which protrude outwardly of the base portion 3 so as to define lugs 9, 19 (see FIG. 3). The bottom surfaces 11, 12 of the lugs 9, 10, respectively, slope downwardly away from base 2 and toward the surface of the tooth on which the bracket is to be mounted so that tieing wires or bands will be securely retained when tied under the lugs 9, 10.

The ceramic bracket has holes 13 formed in the bottom surface thereof and extending into the base portion 3 of the bracket. The holes 13 are to improve the bonding of the bracket to the tooth surface by means of adhesives such as for example the methylmethacrylate system, an acrylic modified epoxy resin, etc. When bonding the bracket to a tooth, the adhesive placed on the lower surface 1 of the ceramic bracket enters into the bores or holes 13, thereby improving the bond between the tooth and the bracket. The holes 13 are particularly important in ceramic brackets of the present invention since such brackets are dense and are therefore otherwise difficult to bond securely to a tooth, or the like.

The ceramic bracket provides a unique physical characteristic. If, for example, one of the lugs 9, 10 of the ceramic bracket becomes broken in use, of if the bracket becomes otherwise damaged, using conventional orthodontic techniques the orthodontist would remove the complete bracket from the tooth and bond a new bracket to the tooth. This is undesirable in that repeated bonding processes may have adverse effects on the tooth surface of the patient. With a ceramic bracket, the damaged portion could be broken off by the orthodontist using pliers, cutters, etc., to leave all or a part of the base portion 2 adhered to the tooth. This forms a base on which a new bracket or other appliance may be adhered. In accordance with the present invention, the holes 13 extending into the rear of the bracket also provide weakened or "breaking" areas in the ceramic bracket whereby the orthodontist is able to more easily cut or break off a remaining lug and/or most of the remaining parts of the broken ceramic bracket by using pliers, cutters or the like. If the portion of the bracket which remains bonded to the tooth does not present a suitable surface for bonding another bracket thereon, the remaining portion of the bracket (which remained adhered to the tooth) is ground down to provide a surface for receiving a new bracket thereon. The new bracket is then bonded directly to the remaining stub of the broken bracket, without requiring rebonding of a bracket to the tooth surface. The above procedures are applicable also when it is desired to replace a bracket with another bracket or with another appliance for reasons other than damage to the original bracket.

If the stub of the broken bracket is removed to a great enough degree, it is possible to expose the portions of the holes or bores 13 which are outermost with respect to the surface of the tooth. In the event that the original adhesive did not travel completely through the length of the holes or bores 13, the open forward ends thereof may then serve to receive adhesive for adhering a new bracket to the stub of the broken bracket, thereby improving the bonding effect.

Figure 5:
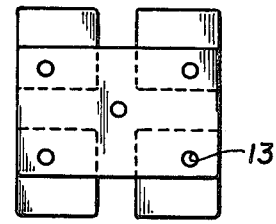
FIG. 5 is a rear view of a modified embodiment of the invention.
Figure 2:
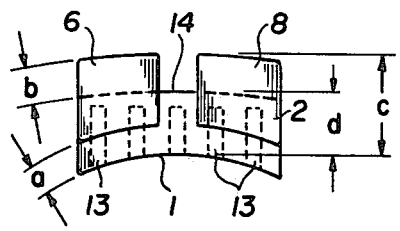
FIG. 2 is a side view (occlusal or gingival) thereof.

The number of holes 13 may be varied. The embodiment of FIGS. 1-4 has eight holes therein. The embodiment of FIGS. 5 and 6, which is identical with that of FIGS. 1-4 except for the number of holes, has five holes 13 therein. The more holes which are placed in the base portion of the ceramic bracket, the greater will be the improvement in bonding effect and the easier it will be to break off the remaining portion of a broken bracket. However, the bracket will be accordingly weakened by adding more holes thereto. The holes 13 may extend to close proximity to the upper surface 14 of the base portion 2 of the bracket. The holes 13 closer to the edges of the base portion 2 may extend so that they intersect a straight line passing through the corners or angular portions 15, 16 (see FIG. 3) of the bracket so that a lug may be more easily broken off by the orthodontist, as desired. Angular portions or corners 15, 16, which may be sharp or rounded, define the intersection of two surfaces which meet at an angle of less than 180°.

It is pointed out that the breaking off of a lug or of the top or outermost part of the bracket by an orthodontist may not only occur when the bracket becomes damaged. There may be instances where it is desired to replace the bracket by another type of orthodontic appliance. In such a case, the orthodontist may break off the top part of the bracket with a pair of pliers or with a cutting device and then, if necessary, grind down the remaining bracket portion to provide a receiving surface for bonding another orthodontic appliance thereto, without requiring rebonding directly to the tooth.

In a typical preferred embodiment shown in FIGS. 1-4, the following dimensions for a ceramic bracket have been found to be suitable.

| | |
|---|---|
| a | 0.018 inches |
| b | 0.025 inches |
| c | 0.065 inches |
| d | 0.040 inches |
| e | 0.132 inches |
| f | from about 0.018-0.024 inches |
| g | 0.023 inches |
| h | 0.082 inches |
| i | 0.025 inches |
| j | 0.026 inches |
| k | 0.026 inches |
| m | 0.046 inches |
| n | 0.046 inches |

In the above embodiment with the dimensions listed above, the holes 13 are approximately 0.025 inches in diameter and about 0.030 inches deep. The specific dimensions of the holes may, of course, vary depending upon manufacturing tolerances and the specific characteristics desired.

Figure 7:
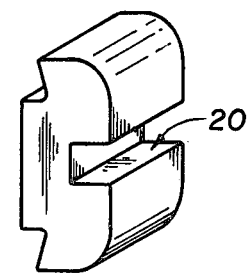
FIG. 7 is a perspective view of another bracket of the invention.
Figure 4:
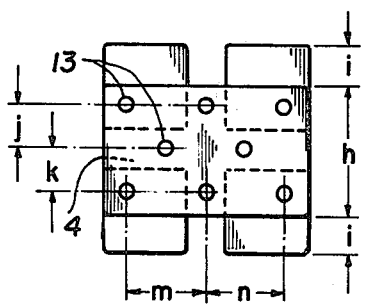
FIG. 4 is a rear view thereof.

The ceramic bracket of the present invention may take other shapes, for example as illustrated in FIG. 7. The arch wire receiving slot 20 in FIG. 7 is about 0.020 by 0.025 inches.

The arch wire slots in the embodiments described herein may have different dimensions, depending upon application. Preferably, a series of brackets having different respective arch wire receiving slot dimensions may be manufactured. As a practical matter, the dimensions of the arch wire receiving slots are generally in the order of from about 0.018-0.022 by 0.025-0.028 inches, the length of the slots corresponding to the width of the brackets.

While the surface 1 of the bracket shown in FIGS. 1-4 is curved, the surface may be flat or any other suitable shape. Also, the external contours of the bracket may be varied.

Figure 8:
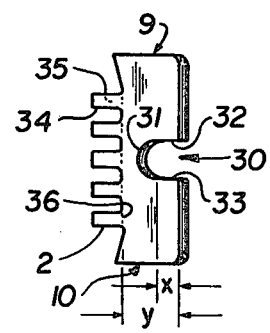
FIG. 8 is a side view (mesial or distal) of a modification of the embodiment of FIGS. 1-4.

FIG. 8 shows a modification of the present invention wherein the arch wire receiving slot 30 has a rounded bottom portion 31. The side walls 32, 33 of the arch wire receiving slot are generally straight and are substantially parallel to each other. The dimension "x" in FIG. 8 is approximately 0.025-0.028 inches. The rounded bottom 31 is a convenient configuration when the bracket is made from ceramic material. Ceramic materials are very hard and machining thereof is difficult. In manufacture of the ceramic bracket, it is possible that the arch wire receiving slot will not be the exact desired dimensions, due to manufacturing tolerances, expansion and contraction, etc. Therefore, the arch wire receiving slot 30 may sometimes be trimmed or exactly sized by running a grinding wheel through the arch wire receiving slot. The grinding wheel generally produces a rounded bottom surface 31. The rounded bottom surface 31 is advantageous from the point of view of strength of the resulting bracket. This is because the sharp corners at the bottom of the arch wire receiving slot are eliminated, which sharp corners are weakening points in the resulting bracket. The rounded bottom surface 31 is preferably molded-in during manufacture.

Since ceramic materials are relatively brittle, it is desired that the lug portions 9, 10 not extend too far from the main body of the bracket. Further, it is desired that the thickness of the lugs 9, 10, in a direction perpendicular to the face of the tooth, as indicated by the dimension "y" in FIG. 8, be greater than one half the overall thickness of the bracket in a direction perpendicular to the face of the tooth. In the preferred embodiment illustrated in the figures, the minimum width of the lugs 9, 10 is approximately 70% of the overall width of the bracket, as is clearly seen in FIG. 3. Also, in the preferred embodiment as shown in FIGS. 1-6 and 8, each of the lugs extends out from the base portion 2 a distance of slightly less than 20% of the overall size of the bracket. This is important to prevent the bracket from breaking during normal use in the mouth. The resulting bracket of the present invention has a high degree of strength, may be manufactured in a practical manner and has a good appearance in the mouth. Moreover, the bracket may be strongly bonded to a tooth.

Referring again to FIG. 8, the holes 13 in the embodiment of FIGS. 1-6 may be replaced by grooves 34 which extend into the base portion of the bracket and which preferably extend along the complete width or length of the base portion. Grooves 35 extend perpendicularly to grooves 34 and are shown by a dashed line in FIG. 8. One set of parallel grooves 34 or 35, or two sets of intersecting grooves may be provided. The grooves may take any shape or arrangement. The grooves 34, 35 may be molded in the article or may be formed later, for example by grinding.

The grooves 34, 35 of FIG. 8, or the holes 13 of FIGS. 1-6 may extend into the base portion 2 a distance corresponding to the approximate point where the lugs 9, 10 extend from the base portion 2. This distance is shown by way of example in FIG. 8. By appropriately gripping the bracket with pliers or cutters, the orthodontist may shear the top portion of the bracket off, leaving the base portion 2 approximately broken along the dashed line 36 shown in FIG. 8.

The arch wire channels for the brackets of FIGS. 1-8 may be angulated relative to the rest of the bracket in any desired direction to produce rotation, tilting or torquing of a tooth. The angulated arch wire channels may be directly molded in their desired orientation or may be machined into their desired orientation.

Figure 9:
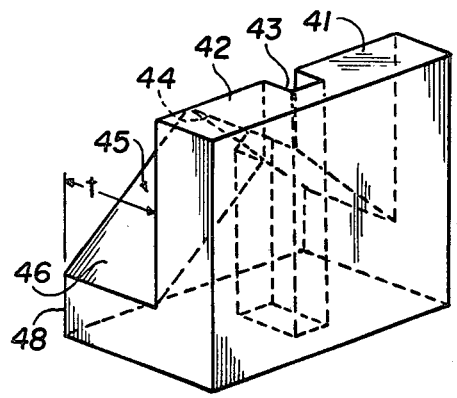
FIGS. 9 and 10 illustrate another embodiment of the invention
Figure 10:
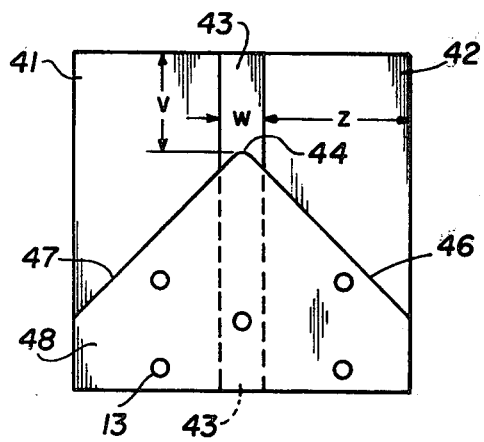
Figure 11:
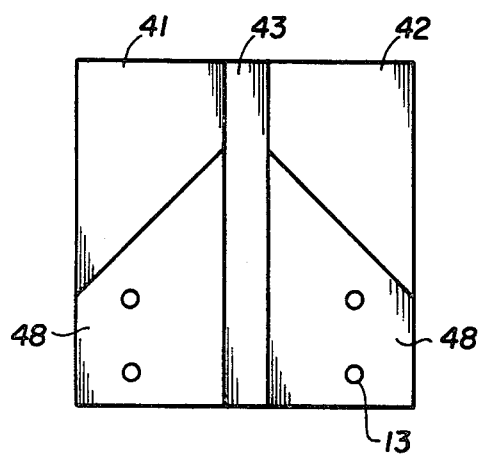
FIG. 11 illustrates a modification of the embodiment of FIGS. 9 and 10.

FIGS. 9 and 10 illustrate a perspective and rear views respectively, of a ceramic light wire bracket. The ceramic light wire bracket of the present invention differs from conventional light wire brackets in that the side arm portions 41, 42 are substantially wider than in the prior art Begg brackets. The channel 43 which runs in the vertical direction of the bracket is substantially the same size as in conventional brackets. Since the overall width of the bracket is so substantial, in accordance with the present invention, a substantially pointed area 44 is provided for contacting the arch wire which is receiving in the arch wire receiving opening 45. The surfaces 46, 47 slope upwardly from the opposite sides of the bracket and meet at point 44. Point 44 may be slightly rounded or even divided as shown in FIG. 11.

Since the width of the side portions 41, 42 is substantial, the ceramic bracket of the present invention has the advantage of having the capability of imparting rotational forces to a tooth via the arch wire.

In a typical embodiment of the ceramic light wire bracket of FIGS. 9 and 10, the dimensions t, v, w and z are approximately as follows:
t: 0.022-0.025 inches
v: 0.35 inches
w: 0.020 inches
z: 0.030 inches
The dimension z is preferably at least 1½ times w.

The above dimensions may vary, depending upon particular requirements. While the surfaces of the bracket of FIGS. 9 and 10 are shown meeting at sharp edges, in the ceramic bracket, the edges are preferably rounded in order to facilitate molding and to reduce the possibility of breakage in the mouth. The channel 43 preferably runs completely through the bracket in the vertical direction.

The surface 48 of the bracket is adhered to the surface of a tooth, and may be curved to conform with the contour of the tooth. The surface 48 preferably also has holes 13 therein to improve adherence to the tooth. Instead of holes 13, the surface 48 may have grooves either in one direction or in intersecting directions, similar to the grooves 34, 35 shown in FIG. 8.

Figure 6:
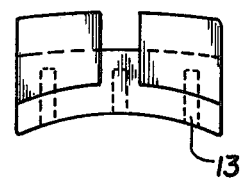
FIG. 6 is a side view (occlusal or gingival) of the modified embodiment of FIG. 5.
Figure 3:
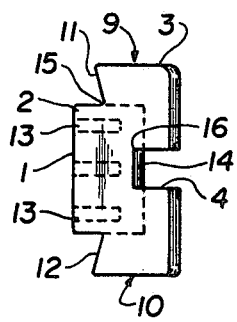
FIG. 3 is a side view (mesial or distal) thereof taken in a direction perpendicular to the side view of FIG. 2.
Figure 12:
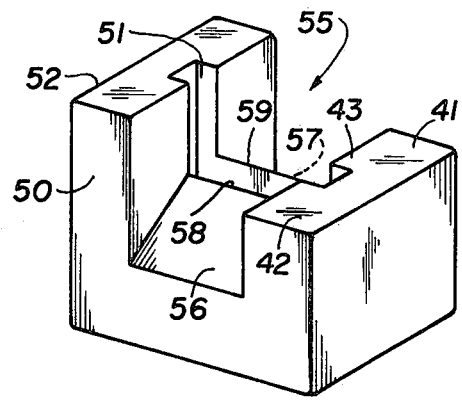
FIGS. 12 and 13 are perspective and top views, respectively, of a modified light wire bracket of the present invention.
Figure 13:
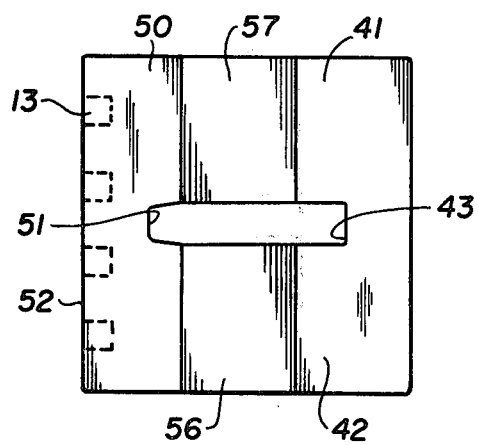
Figure 14:
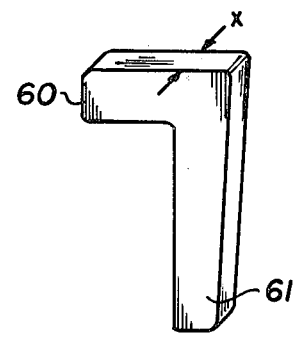
FIG. 14 illustrates a typical pin for use with the brackets of FIGS. 9-13.

Referring to FIGS. 12 and 13, a further light wire bracket of the present invention, which may have substantially similar dimensions as the bracket of FIGS. 9 and 10, comprises a rear upstanding portion 50 having a pin-receiving groove 51 formed therein. Upstanding rear portion 50 also has a plurality of holes or other indentations 13 formed in the rear surface thereof to improve adhesion to a tooth. The rear surface 52 of upstanding portion 50 may be curved, for example as illustrated in FIG. 6, to better conform to the outer surface of a tooth to improve adhesion. Upwardly sloping surfaces 56,57 form respectively pointed or slightly rounded upper surfaces 58,59, respectively. Surfaces 58,59 substantially comprise the "point contact" for a light wire for use with the bracket of the present invention. After insertion of the wire into the arch wire receiving opening so that it bears upon surfaces 58 and 59, a pin, which may be a conventional light-wire type pin as shown in FIG. 14 is inserted into the groove 43, the forward end portion 60 of the pin being engaged in groove 51 to more firmly lock the wire in place by, for example, bending over the bottom of leg 61 of the pin of FIG. 14 after insertion into channel 43. When using the bracket of FIGS. 12 and 13 with a rectangular arch wire, the pin firmly retains the rectangular arch wire in the arch wire receiving opening 55 of the bracket. The front end of the pin 60 may extend downwardly into groove 51 and bear upon a side edge of a wire inserted in the arch wire receiving opening 55 of the bracket.

The bracket of FIGS. 12 and 13 may be fabricated with a solid rear upstanding wall portion 50, not having a groove 51 therein. Alternatively, the bracket of FIGS. 9 and 10 may be provided with an upstanding rear wall 50, with or without the rear groove 51. In this modification, the upwardly sloping surfaces 46,47 present only a single bearing surface 44.

The ceramic brackets are formed of a ceramic material which is a naturally white or off-white composition or a composition which may be colored to the desired shade of white, e.g. with a pigment. It may also be transparent or translucent depending on ceramic composition. The ceramic has a tensile strength of at least about 15,000 psi, preferably at least about 18,000 psi, and more preferably above about 18,500 psi. The modulus of elasticity should be greater than about $15 \times 10^6$ psi, preferably greater than about $32 \times 10^6$ and more preferably above about $42 \times 10^6$ psi. The impact resistance should be at least about 5, preferably more than about 6.3, and more preferably at least about 6.5 (Charpy). The hardness should be at least about 9 on the Mohs scale, and preferably above 9. The ceramic should have a good surface finish as fired.

The ceramic preferably also has a flexural strength greater than about 42,000 psi and preferably more than about 46,000 psi. The compression strength of most dense ceramics is suitable; preferably in excess of about 230,000 psi, and more preferably in excess of about 275,000 psi.

The ceramic should be chemically resistant to the fluids and liquid containing materials present in the mouth when the person is eating and also to these materials present when the person is not eating. These readily can be determined by the known procedures for testing the long term stability of dental materials in the fluids present in the human mouth. The ceramic is preferably also substantially impervious to water.

The high alumina ceramics are preferred. The preferred alumina ceramics are at least about 85% by weight $Al_2O_3$, and preferably at least 90% $Al_2O_3$, e.g., about 90–99.9% $Al_2O_3$. The remaining constituents may include silica and a fluxing agent, such as CaO, or a corresponding sodium or potassium, or barium oxide, or compound, including small amounts of talc or clay and lime. The constituents are desirable to provide a lower melting phase (binder) permitting liquid phase sintering, resulting in the production of a dense ceramic. The ceramics are also preferably very fine grained which is conducive to high mechanical properties and smooth surface finish. Additives which induce fine grain formation and, particularly MgO, are preferred. The preferred compositions contain, in addition to the $Al_2O_3$ as aforesaid, CaO, $SiO_2$, and MgO.

The presently preferred ceramic is an alumina ceramic containing about 93.5% $Al_2O_3$, with the remainder, the binder, consisting essentially of CaO, $SiO_2$, and MgO, which binder phase may be referred to as a magnesium calcium silicate. The fired ceramic has a tensile strength of about 18,500 psi, a modulus of elasticity of about $42.5 \times 10^6$ psi, a Charpy impact resistance of about 6.5–6.8, a flexural strength of about 46,500 psi, a compression strength of about 280,000, and an average coefficient of thermal expansion in the range of 25°–200° C. of about $6.18 \times 10^{-6}$ cm/cm/°C. Its hardness on the Mohs scale is in excess of 9. It is a pleasing slightly off-white color.

The high alumina ceramic described in the preceding paragraph may be fabricated using conventional ceramic techniques for example a ceramic slip is injection molded or pressed to form a green bracket which is then fired e.g., at a temperature preferably in the range of about 1575°–1675° C. The bracket will shrink during sintering. The holes 13 are formed when the green bracket is shaped. The grooved indentation may also be formed in the green bracket, or may be subsequently cut and/or finished with a diamond cutting wheel.

Although the high alumina ceramics are preferred, ceramics of comparable properties produced from other ceramic compositions, e.g., zircon (zirconia silicate), stabilized zirconia, titania, and polycrystalline glass-ceramics can also be used when compositions and processing conditions are selected to produce a ceramic having a desired combination of properties of the ceramic brackets of the present invention.

While the invention has been described above with respect to particular embodiments, various modifications and alterations may be made within the scope of the invention, as set forth in the claims. For example, the number of grooves shown in FIG. 8 and the number of holes 13 shown in the other figures is merely exemplary. Also, the particular contours of the bracket may be varied, as well as the dimensions.

I claim:

1. A substantially solid ceramic orthodontic bracket formed substantially completely of said ceramic, comprising a shaped article having a first surface adapted to be affixed to a surface of a tooth, the side of said article which is opposed to said first surface have a groove-like indentation therein for receiving an arch wire or the like, the article further comprising at least two outwardly extending lugs which extend from opposite side surfaces of said article, said ceramic being substantially white in color and having a tensile strength of at least about 15,000 psi, a modulus of elasticity in excess of about $15 \times 10^6$ psi, a Charpy impact resistance of at least about 5, and a hardness of at least about 9 on the Mohs scale.

2. The ceramic bracket of claim 1 further comprising a plurality of rear indentations extending into said bracket from said first surface.

3. The ceramic bracket of claim 2 wherein said rear indentations extend into said first surface adjacent the point where a lug extends from said article.

4. The ceramic bracket of claim 2 wherein said rear indentations are holes.

5. The ceramic bracket of claim 2 wherein said rear indentations are elongated grooves extending in at least one direction.

6. The ceramic bracket of claim 5 wherein said grooves comprise intersecting grooves.

7. The ceramic bracket of claim 2 wherein said lug froms a first angular portion (15) relative to said article and said arch wire receiving grooved indentation forms a second angular portion (16) interior of said article, said rear indentations extending into said bracket from said first surface a distance sufficient that a substantially straight line interconnecting said angular portions (15,16) passes through at least a portion of said indentations.

8. The ceramic bracket of claim 3 wherein said lug forms a first angular portion (15) relative to said article and said arch wire receiving grooved indentation forms a second angular portion (16) interior of said article, said rear indentations extending into said bracket from said first surface a distance sufficient that a substantially straight line interconnecting said angular portions (15,16) passes through at least a portion of said indentations.

9. The ceramic bracket of claim 3 wherein said rear indentations extend into said bracket from said first surface for a distance of at least $\frac{1}{3}$ the distance between said first surface and said side opposed to said first surface.

10. The ceramic bracket of claim 1 wherein said first surface is curved so as to substantially conform to an outer surface of a tooth.

11. The ceramic bracket of claim 1, wherein said arch wire receiving groove-like indentation has a rounded bottom surface.

12. The ceramic bracket of any one of claims 1–3 or 7–9 wherein said ceramic is selected from the group consisting of alumina ceramics containing about 85% alumina, zircon ceramics, zirconia ceramics, and titania ceramics.

13. The ceramic bracket of any one of claims 1–3 or 7–9 containing at least about 85% by weight $Al_2O_3$, a fine-grain additive, and a flux constituent to provide a lower-melting phase which formed a liquid phase during sintering resulting in the formation of a fine-grained dense ceramic.

14. A substantially solid ceramic orthodontic bracket formed substantially completely of said ceramic, comprising a shaped article having a first surface adapted to be fixed to a surface of a tooth, an indentation in said article for receiving an arch wire or the like and a pin-receiving opening extending adjacent said arch wire receiving indentation and extending substantially perpendicularly to said arch wire receiving indentation, said shaped article further comprising surface means forming at least a portion of a surface of said arch wire receiving indentation and defining an arch wire contact surface which is a substantially point contact surface adjacent said pin-receiving opening, said ceramic being substantially white in color and having a tensile strength of at least about 15,000 psi, a modulus of elasticity in excess of about $15 \times 10^6$ psi, a Charpy impact resistance of at least about 5, and a hardness of at least about 9 on the Mohs scale.

15. The ceramic bracket of claim 14 wherein said substantially point contact surface is in communication with said pin-receiving opening.

16. The ceramic bracket of claim 14 wherein said substantially point contact surface is a slightly rounded surface.

17. The ceramic bracket of claim 14 wherein said surface means which defines said substantially point contact surface comprises at least two inclined surfaces which incline upwardly from the ends of said arch wire receiving indentation and which cooperate to form said substantially point contact surface interior of the ends of said arch wire receiving indentation.

18. The ceramic bracket of claim 17 wherein said at least two surfaces are spaced from each other in the vicinity of said pin-receiving opening, the spaced apart ends together forming two closely spaced contact surfaces which together form said substantially point contact surface.

19. The ceramic bracket of claim 14 wherein said substantially point contact surface comprises at least two closely spaced contact surfaces which together form said substantially point contact surface.

20. The ceramic bracket of claim 14 wherein said first surface extends above said substantially point contact surface and forms at least one wall of said arch wire receiving indentation.

21. The ceramic bracket of claim 20 comprising a further pin-receiving opening in said at least one wall and which is opposed to said first-mentioned pin-receiving opening.

22. The ceramic bracket of claim 21 wherein said pin-receiving openings extend substantially perpendicularly to said arch wire receiving indentation and are located on opposite sides of said arch wire receiving opening in the buccal-lingual direction.

23. The ceramic bracket of claim 14 further comprising surface means adjacent said pin-receiving opening and partially defining said arch wire receiving indentation, said surface means extending a distance substantially greater than the width of said pin-receiving opening in the longitudinal direction of said indentation for defining bearing surfaces for an arch wire or the like.

24. The ceramic bracket of claim 14 comprising a plurality of indentations extending into said bracket from said first surface.

25. The ceramic bracket of claim 24 wherein said indentations comprise a plurality of holes.

26. The ceramic bracket of claim 24 wherein said indentations comprise a plurality of grooves in said first surface.

27. The ceramic bracket of claim 26 wherein said grooves comprise a plurality of intersecting grooves.

28. The ceramic bracket of any one of claims 14–22 wherein said ceramic is selected from the group consisting of alumina ceramics containing about 85% alumina, zircon ceramics, zirconia ceramics, and titania ceramics.

29. The ceramic bracket of any of claims 14–22 containing at least about 85% by weight $Al_2O_3$, a fine-grain additive, and a flux constituent to provide a lower-melting phase which formed a liquid phase during sintering resulting in the formation of a fine-grained dense ceramic.

* * * * *